(12) United States Patent
Strop et al.

(10) Patent No.: US 12,290,570 B2
(45) Date of Patent: May 6, 2025

(54) ANTIBODY COMPRISING A GLUTAMINE-CONTAINING LIGHT CHAIN C-TERMINAL EXTENSION, CONJUGATES THEREOF, AND METHODS AND USES

(71) Applicant: BRISTOL-MYERS SQUIBB COMPANY, Princeton, NJ (US)

(72) Inventors: Pavel Strop, San Mateo, CA (US); Chetana Rao-Naik, Walnut Creek, CA (US); Xiaodi Deng, San Mateo, CA (US); Paul O. Sheppard, Granite Falls, WA (US); Patrick G. Holder, Piedmont, CA (US); Sayumi Yamazoe, Mountain View, CA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 1010 days.

(21) Appl. No.: 17/297,796

(22) PCT Filed: Nov. 25, 2019

(86) PCT No.: PCT/US2019/062913
§ 371 (c)(1),
(2) Date: May 27, 2021

(87) PCT Pub. No.: WO2020/112588
PCT Pub. Date: Jun. 4, 2020

(65) Prior Publication Data
US 2022/0016260 A1   Jan. 20, 2022

Related U.S. Application Data

(60) Provisional application No. 62/773,708, filed on Nov. 30, 2018.

(51) Int. Cl.
*A61K 47/68* (2017.01)
*C07K 16/18* (2006.01)

(52) U.S. Cl.
CPC ...... *A61K 47/6851* (2017.08); *A61K 47/6811* (2017.08); *C07K 16/18* (2013.01)

(58) Field of Classification Search
None
See application file for complete search history.

(56) References Cited

U.S. PATENT DOCUMENTS

| | | |
|---|---|---|
| 6,322,996 B1 | 11/2001 | Sato et al. |
| 8,865,875 B2 | 10/2014 | Liu et al. |
| 9,427,478 B2 | 8/2016 | Bregeon et al. |
| 9,676,871 B2 | 6/2017 | Strop et al. |
| 9,717,803 B2 | 8/2017 | Bregeon et al. |
| 2005/0136491 A1 | 6/2005 | Chen et al. |
| 2007/0184537 A1 | 8/2007 | Schibli et al. |
| 2011/0184147 A1 | 7/2011 | Kamiya et al. |
| 2015/0284713 A1 | 10/2015 | Fischer et al. |
| 2016/0114056 A1 | 4/2016 | Bregeon |
| 2016/0193356 A1 | 7/2016 | Farias et al. |
| 2017/0008970 A1 | 1/2017 | Babcook et al. |
| 2018/0037921 A1 | 2/2018 | Rao-naik et al. |
| 2019/0099506 A1 | 4/2019 | Smith et al. |

FOREIGN PATENT DOCUMENTS

| | | |
|---|---|---|
| WO | 2017025179 A1 | 2/2017 |
| WO | 2017059158 A1 | 4/2017 |

OTHER PUBLICATIONS

Ando et al; Agri. Biol. Chem;_"Purification and Characteristics of a Novel Transglutaminase Derived From Microorganisms"; vol. 53; pp. 2613-2617; 1989.
Dennler et al.; Bioconjug. Chem; "Transglutaminase-Based Chemo-Enzymatic Conjugation Approach Yields Homogeneous Antibody-Drug Conjugates"; vol. 25; pp. 569-578; 2014.
Fontana, et al., Advanced Drug Delivery Reviews; "Site-specific modification and PEGylation of pharmaceutical proteins mediated by transglutaminase"; vol. 60; pp. 13-28; 2008.
Gerber et al.; Nat. Prod. Rep.; "The antibody-drug conjugate: an enabling modality for natural product-based cancer therapeutics"; vol. 30; pp. 625-639; 2013.
Hayura Sato; Advanced Drug Delivery; "Enzymatic procedure for site-specific pegylation of proteins"; vol. 54, pp. 487-504; 2002.
Innate Pharma; "A New Site Specific Antibody Conjugation Using Bacterial Transglutaminase, Presentation at ADS Summit"; pp. 01-29; Oct. 13, 2013.
Jeger, et al.; Agew Chemistry Intl.; "Site-Specific and Stoichiometric Modification of Antibodies by Bacterial Transglutaminase"; vol. 49; pp. 9995-9997; 2010.
Lin et al; JACS; "Transglutaminase-Catalyzed Site-Specific Conjugation of Small-Molecule Probes to Proteins in Vitro and on the Surface of Living Cells"; vol. 128; pp. 4542-4543; Mar. 16, 2006.
Mero et al.; Bioconjugate Chemistry; "Transflutaminase-Mediated PEGylation of Proteins: Direct Indentification of the Sites of Protein Modification by Mass Spectrometry using a Novel Monodisperse PEG"; vol. 20; pp. 384-389; 2009.
Mindt et al.; Bioconjugate Chemistry; "Modification of Different IgG1 Antibodies via Glutamine and Lysine using Bacterial and Human Tissue Transglutaminase"; vol. 19; pp. 271-278; 2008.
Ohtsuka et al.; Biosci. Biotechnol. Biochem.; "Comparision of Substrate Specificities of Transglutaminases Using Synthetic Peptides as Acyl Donors"; vol. 64; pp. 2608-2613; 2000.
PCT ISR Dated Feb. 28, 2020, Feb. 28, 2020, 1_18, ISA_EP.
Strop, et al.; Chemisry & Biology; "Location Matters: Site of Conjugation Modulates Stability and Pharmacokinetics of Antibody Drug Conjugates"; vol. 20; pp. 161-167; 2013.
Sugimura et al.; Archives of BioChemistry and Biophysics; "Identification of Preferred Substrate Sequences of Microbial Transglutaminase from Streptomyces Mobargensis Using a Phage-Displayed Peptide Library"; vol. 477; pp. 379-383; 2008.
Sugimura, et al.; Journal of Biotechnology; "Novel site-specific immobilization of a functional protein using a preferred substrate sequence for transglutaminase 2"; vol. 131; pp. 121-127; 2007.

*Primary Examiner* — Nora M Rooney
(74) *Attorney, Agent, or Firm* — Gregory R. Bellomy

(57) ABSTRACT

An antibody has a glutamine-containing extension at the C-terminus of a light chain thereof, making it suitable for conjugation via transglutaminase-mediated transamidation.

Figure 1:

23 Claims, 2 Drawing Sheets
Specification includes a Sequence Listing.

Preparation of Antibody Conjugate Using Transglutaminase (BTG)

SEQUENCE LISTING

```
<160> NUMBER OF SEQ ID NOS: 40

<210> SEQ ID NO 1
<211> LENGTH: 8
<212> TYPE: PRT
<213> ORGANISM: Artificial Sequence
<220> FEATURE:
<223> OTHER INFORMATION: C-Terminal Extension

<400> SEQUENCE: 1

Gly Gly Val Leu Gln Arg Ala Ser
1               5

<210> SEQ ID NO 2
<211> LENGTH: 8
<212> TYPE: PRT
<213> ORGANISM: Artificial Sequence
<220> FEATURE:
<223> OTHER INFORMATION: C-Terminal Extension

<400> SEQUENCE: 2

Gly Gly Val Leu Gln Gly Ala Ser
1               5

<210> SEQ ID NO 3
<211> LENGTH: 8
<212> TYPE: PRT
<213> ORGANISM: Artificial Sequence
<220> FEATURE:
<223> OTHER INFORMATION: C-Terminal Extension

<400> SEQUENCE: 3

Gly Gly Val Leu Gln Arg Pro Ser
1               5

<210> SEQ ID NO 4
<211> LENGTH: 8
<212> TYPE: PRT
<213> ORGANISM: Artificial Sequence
<220> FEATURE:
<223> OTHER INFORMATION: C-Terminal Extension

<400> SEQUENCE: 4

Gly Gly Val Leu Gln Gly Pro Ser
1               5

<210> SEQ ID NO 5
<211> LENGTH: 8
<212> TYPE: PRT
<213> ORGANISM: Artificial Sequence
<220> FEATURE:
<223> OTHER INFORMATION: C-Terminal Extension

<400> SEQUENCE: 5

Gly Gly Val Leu Gln Ser Pro Ser
1               5
```

```
<210> SEQ ID NO 6
<211> LENGTH: 8
<212> TYPE: PRT
<213> ORGANISM: Artificial Sequence
<220> FEATURE:
<223> OTHER INFORMATION: C-Terminal Extension

<400> SEQUENCE: 6

Gly Gly Val Leu Gln Tyr Ala Ser
1               5

<210> SEQ ID NO 7
<211> LENGTH: 10
<212> TYPE: PRT
<213> ORGANISM: Artificial Sequence
<220> FEATURE:
<223> OTHER INFORMATION: C-Terminal Extension

<400> SEQUENCE: 7

Gly Gly Gly Gly Val Leu Gln Arg Ala Ser
1               5                   10

<210> SEQ ID NO 8
<211> LENGTH: 10
<212> TYPE: PRT
<213> ORGANISM: Artificial Sequence
<220> FEATURE:
<223> OTHER INFORMATION: C-Terminal Extension

<400> SEQUENCE: 8

Gly Gly Gly Gly Val Leu Gln Gly Ala Ser
1               5                   10

<210> SEQ ID NO 9
<211> LENGTH: 10
<212> TYPE: PRT
<213> ORGANISM: Artificial Sequence
<220> FEATURE:
<223> OTHER INFORMATION: C-Terminal Extension

<400> SEQUENCE: 9

Gly Gly Gly Gly Val Leu Gln Arg Pro Ser
1               5                   10

<210> SEQ ID NO 10
<211> LENGTH: 10
<212> TYPE: PRT
<213> ORGANISM: Artificial Sequence
<220> FEATURE:
<223> OTHER INFORMATION: C-Terminal Extension

<400> SEQUENCE: 10

Gly Gly Gly Gly Val Leu Gln Gly Pro Ser
1               5                   10

<210> SEQ ID NO 11
<211> LENGTH: 10
<212> TYPE: PRT
<213> ORGANISM: Artificial Sequence
<220> FEATURE:
<223> OTHER INFORMATION: C-Terminal Extension

<400> SEQUENCE: 11

Gly Gly Gly Gly Val Leu Gln Ser Pro Ser
1               5                   10
```

```
<210> SEQ ID NO 12
<211> LENGTH: 10
<212> TYPE: PRT
<213> ORGANISM: Artificial Sequence
<220> FEATURE:
<223> OTHER INFORMATION: C-Terminal extension

<400> SEQUENCE: 12

Gly Gly Gly Gly Val Leu Gln Tyr Ala Ser
1               5                   10

<210> SEQ ID NO 13
<211> LENGTH: 6
<212> TYPE: PRT
<213> ORGANISM: Artificial Sequence
<220> FEATURE:
<223> OTHER INFORMATION: C-Terminal Extension

<400> SEQUENCE: 13

Val Leu Gln Tyr Ala Ser
1               5

<210> SEQ ID NO 14
<211> LENGTH: 8
<212> TYPE: PRT
<213> ORGANISM: Artificial Sequence
<220> FEATURE:
<223> OTHER INFORMATION: C-Terminal Extension

<400> SEQUENCE: 14

Gly Gly Val Leu Gln Arg Gln Ser
1               5

<210> SEQ ID NO 15
<211> LENGTH: 8
<212> TYPE: PRT
<213> ORGANISM: Artificial Sequence
<220> FEATURE:
<223> OTHER INFORMATION: C-Terminal Extension

<400> SEQUENCE: 15

Gly Gly Val Leu Gln Gly Gln Ser
1               5

<210> SEQ ID NO 16
<211> LENGTH: 10
<212> TYPE: PRT
<213> ORGANISM: Artificial Sequence
<220> FEATURE:
<223> OTHER INFORMATION: C-Terminal Extension

<400> SEQUENCE: 16

Gly Gly Val Leu Gln Arg Gln Arg Pro Ser
1               5                   10

<210> SEQ ID NO 17
<211> LENGTH: 10
<212> TYPE: PRT
<213> ORGANISM: Artificial Sequence
<220> FEATURE:
<223> OTHER INFORMATION: C-Terminal Extension

<400> SEQUENCE: 17

Gly Gly Val Leu Gln Gly Gln Gly Pro Ser
1               5                   10
```

-continued

```
<210> SEQ ID NO 18
<211> LENGTH: 10
<212> TYPE: PRT
<213> ORGANISM: Artificial Sequence
<220> FEATURE:
<223> OTHER INFORMATION: C-Terminal Extension

<400> SEQUENCE: 18

Gly Gly Val Leu Gln Ser Gln Ser Pro Ser
1               5                   10

<210> SEQ ID NO 19
<211> LENGTH: 8
<212> TYPE: PRT
<213> ORGANISM: Artificial Sequence
<220> FEATURE:
<223> OTHER INFORMATION: C-Terminal Extension

<400> SEQUENCE: 19

Gly Gly Val Leu Gln Tyr Gln Ser
1               5

<210> SEQ ID NO 20
<211> LENGTH: 10
<212> TYPE: PRT
<213> ORGANISM: Artificial Sequence
<220> FEATURE:
<223> OTHER INFORMATION: C-Terminal extension

<400> SEQUENCE: 20

Gly Gly Gly Gly Val Leu Gln Arg Gln Ser
1               5                   10

<210> SEQ ID NO 21
<211> LENGTH: 10
<212> TYPE: PRT
<213> ORGANISM: Artificial Sequence
<220> FEATURE:
<223> OTHER INFORMATION: C-Terminal Extension

<400> SEQUENCE: 21

Gly Gly Gly Gly Val Leu Gln Gly Gln Ser
1               5                   10

<210> SEQ ID NO 22
<211> LENGTH: 12
<212> TYPE: PRT
<213> ORGANISM: Artificial Sequence
<220> FEATURE:
<223> OTHER INFORMATION: C-Terminal extension

<400> SEQUENCE: 22

Gly Gly Gly Gly Val Leu Gln Arg Gln Arg Pro Ser
1               5                   10

<210> SEQ ID NO 23
<211> LENGTH: 12
<212> TYPE: PRT
<213> ORGANISM: Artificial Sequence
<220> FEATURE:
<223> OTHER INFORMATION: C-Terminal extension

<400> SEQUENCE: 23

Gly Gly Gly Gly Val Leu Gln Gly Gln Gly Pro Ser
1               5                   10

<210> SEQ ID NO 24
```

```
<211> LENGTH: 12
<212> TYPE: PRT
<213> ORGANISM: Artificial Sequence
<220> FEATURE:
<223> OTHER INFORMATION: C-Terminal Extension

<400> SEQUENCE: 24

Gly Gly Gly Gly Val Leu Gln Ser Gln Ser Pro Ser
1               5                   10

<210> SEQ ID NO 25
<211> LENGTH: 10
<212> TYPE: PRT
<213> ORGANISM: Artificial Sequence
<220> FEATURE:
<223> OTHER INFORMATION: C-Terminal Extension

<400> SEQUENCE: 25

Gly Gly Gly Gly Val Leu Gln Tyr Gln Ser
1               5                   10

<210> SEQ ID NO 26
<211> LENGTH: 6
<212> TYPE: PRT
<213> ORGANISM: Artificial Sequence
<220> FEATURE:
<223> OTHER INFORMATION: C-Terminal Extension

<400> SEQUENCE: 26

Val Leu Gln Tyr Gln Ser
1               5

<210> SEQ ID NO 27
<211> LENGTH: 451
<212> TYPE: PRT
<213> ORGANISM: Homo sapiens
<220> FEATURE:
<221> NAME/KEY: MISC_FEATURE
<223> OTHER INFORMATION: Anti-mesothelin antibody heavy chain

<400> SEQUENCE: 27

Gln Val His Leu Val Glu Ser Gly Gly Val Val Gln Pro Gly Arg
1               5                   10                  15

Ser Leu Arg Leu Ser Cys Val Ala Ser Gly Ile Thr Phe Arg Ile Tyr
                20                  25                  30

Gly Met His Trp Val Arg Gln Ala Pro Gly Lys Gly Leu Glu Trp Val
            35                  40                  45

Ala Val Leu Trp Tyr Asp Gly Ser His Glu Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Asp Gly Asp Tyr Tyr Ser Gly Ser Pro Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
```

165                 170                 175
Ala Val Leu Gln Ser Ser Gly Leu Tyr Ser Leu Ser Ser Val Val Thr
                    180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Arg Val Glu Pro Lys Ser
            210                 215                 220

Cys Asp Arg Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 28
<211> LENGTH: 214
<212> TYPE: PRT
<213> ORGANISM: Homo sapiens
<220> FEATURE:
<221> NAME/KEY: MISC_FEATURE
<223> OTHER INFORMATION: Anti-mesothelin antibody kappa chain

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 29
<211> LENGTH: 9
<212> TYPE: PRT
<213> ORGANISM: Artificial Sequence
<220> FEATURE:
<223> OTHER INFORMATION: C-Terminal Extension

<400> SEQUENCE: 29

Gly Gly Val Leu Gln Val Leu Gln Ser
1               5

<210> SEQ ID NO 30
<211> LENGTH: 10
<212> TYPE: PRT
<213> ORGANISM: Artificial Sequence
<220> FEATURE:
<223> OTHER INFORMATION: C-Terminal Extension

<400> SEQUENCE: 30

Gly Gly Val Leu Gln Gly Val Leu Gln Ser
1               5                   10

<210> SEQ ID NO 31
<211> LENGTH: 11
<212> TYPE: PRT
<213> ORGANISM: Artificial Sequence
<220> FEATURE:
<223> OTHER INFORMATION: C-Terminal Extension

<400> SEQUENCE: 31

Gly Gly Val Leu Gln Gly Gly Val Leu Gln Ser
1               5                   10

<210> SEQ ID NO 32
<211> LENGTH: 11
<212> TYPE: PRT
<213> ORGANISM: Artificial Sequence
<220> FEATURE:
<223> OTHER INFORMATION: C-Terminal Extension

<400> SEQUENCE: 32
```

-continued

Gly Gly Val Leu Gln Val Leu Gln Gly Pro Ser
1               5                   10

<210> SEQ ID NO 33
<211> LENGTH: 11
<212> TYPE: PRT
<213> ORGANISM: Artificial Sequence
<220> FEATURE:
<223> OTHER INFORMATION: C-Terminal Extension

<400> SEQUENCE: 33

Gly Gly Val Leu Gln Gly Gly Gln Gly Pro Ser
1               5                   10

<210> SEQ ID NO 34
<211> LENGTH: 12
<212> TYPE: PRT
<213> ORGANISM: Artificial Sequence
<220> FEATURE:
<223> OTHER INFORMATION: C-Terminal Extension

<400> SEQUENCE: 34

Gly Gly Val Leu Gln Gly Gly Gly Gln Gly Pro Ser
1               5                   10

<210> SEQ ID NO 35
<211> LENGTH: 11
<212> TYPE: PRT
<213> ORGANISM: Artificial Sequence
<220> FEATURE:
<223> OTHER INFORMATION: C-Terminal Extension

<400> SEQUENCE: 35

Gly Gly Gly Gly Val Leu Gln Val Leu Gln Ser
1               5                   10

<210> SEQ ID NO 36
<211> LENGTH: 12
<212> TYPE: PRT
<213> ORGANISM: Artificial Sequence
<220> FEATURE:
<223> OTHER INFORMATION: C-Terminal Extension

<400> SEQUENCE: 36

Gly Gly Gly Gly Val Leu Gln Gly Val Leu Gln Ser
1               5                   10

<210> SEQ ID NO 37
<211> LENGTH: 13
<212> TYPE: PRT
<213> ORGANISM: Artificial Sequence
<220> FEATURE:
<223> OTHER INFORMATION: C-Terminal Extension

<400> SEQUENCE: 37

Gly Gly Gly Gly Val Leu Gln Gly Gly Val Leu Gln Ser
1               5                   10

<210> SEQ ID NO 38
<211> LENGTH: 13
<212> TYPE: PRT
<213> ORGANISM: Artificial Sequence
<220> FEATURE:
<223> OTHER INFORMATION: C-Terminal Extension

<400> SEQUENCE: 38

Gly Gly Gly Gly Val Leu Gln Val Leu Gln Gly Pro Ser

```
<210> SEQ ID NO 39
<211> LENGTH: 13
<212> TYPE: PRT
<213> ORGANISM: Artificial Sequence
<220> FEATURE:
<223> OTHER INFORMATION: C-Terminal Extension

<400> SEQUENCE: 39

Gly Gly Gly Gly Val Leu Gln Gly Gly Gln Gly Pro Ser
1               5                   10

<210> SEQ ID NO 40
<211> LENGTH: 14
<212> TYPE: PRT
<213> ORGANISM: Artificial Sequence
<220> FEATURE:
<223> OTHER INFORMATION: C-Terminal Extension

<400> SEQUENCE: 40

Gly Gly Gly Gly Val Leu Gln Gly Gly Gly Gln Gly Pro Ser
1               5                   10
```

ANTIBODY COMPRISING A GLUTAMINE-CONTAINING LIGHT CHAIN C-TERMINAL EXTENSION, CONJUGATES THEREOF, AND METHODS AND USES

CROSS-REFERENCE TO RELATED APPLICATIONS

This application claims the benefit under 35 U.S.C. § 119(e) of U.S. Provisional Application Ser. No. 62/773,708, filed Nov. 30, 2018; the disclosure of which is incorporated herein by reference.

SEQUENCE LISTING

Incorporated herein by reference in its entirety is a Sequence Listing named "191017_SEQT_13142WOPCT_YC.txt," comprising SEQ ID NO:1 through SEQ ID NO:40, which include nucleic acid and/or amino acid sequences disclosed herein. The Sequence Listing has been submitted herewith in ASCII text format via EFS-Web, and thus constitutes both the paper and computer readable form thereof. The Sequence Listing was first created using PatentIn 3.5 on Oct. 26, 2018, and is approximately 14 KB in size.

BACKGROUND OF THE DISCLOSURE

This disclosure relates to modified antibodies conjugatable by the enzyme transglutaminase and conjugates made from such antibodies.

A type of biologic that has attracted intense current interest is one in which an antibody is covalently linked to a partner molecule ("conjugate" or "immunoconjugate"). Thus, a conjugate comprises three components: (1) the antibody, (2) the partner molecule, and (3) a linker covalently joining the first two components.

The partner molecule can be a therapeutic agent such as an anti-cancer drug, an adjuvant, another protein, or a radioisotope. The antibody is one whose antigen is expressed by a target cell or tissue. The antibody, through its binding to the antigen, serves to deliver the conjugate to the target. Once there, cleavage of the covalent link or degradation of the antibody results in the release of the therapeutic agent at the target location. Conversely, while the conjugate is circulating in the blood system, the therapeutic agent is held inactive because of its covalent linkage to the antibody, reducing the risk of side effects. For a review on conjugates in anti-cancer treatment, see Gerber et al. 2013.

Alternatively to a therapeutic agent, the partner molecule can be an assay agent for diagnosing, locating a disease site, or monitoring of a medical condition. In such instance, the assay agent can be, for example, biotin, a fluorescent label, a radioactive label, or a deuterated polymer. Smith et al. 2019 discloses a conjugate comprising a deuterated polymer for MRI imaging. In such instance, cleavage of the linker at the target site is not necessary and may in fact be undesirable. For such use, the linker can be designed to be of the non-cleavable type.

A key step in the preparation of a conjugate is the covalent joining step, also referred to as the conjugation step. Many methods having been disclosed for effecting conjugation. One that has attracted substantial recent interest is conjugation mediated by the enzyme transglutaminase (EC 2.3.2.13).

Many transglutaminase variants are known, either produced naturally by different organisms or made by bioengineering. One commonly used in the food industry for texturing proteins is *Streptomyces mobaraensis* transglutaminase, obtained by fermentation or recombinant expression. Herein, the term "transglutaminase" is used generically unless a specific type or source is indicated.

Transglutaminase forms an amide bond between the carboxamide side chain of a glutamine (the amine acceptor, or, reciprocally, the acyl donor) and the ε-amino group of a lysine (the amine donor, or, reciprocally, the acyl acceptor). Specificity-wise, transglutaminase is selective regarding the glutamine residue, requiring it to be located in a flexible part of a protein loop and flanked by certain amino acids, but is promiscuous regarding the lysine residue, for example readily accepting the amino group of an alkyleneamino compound as a lysine ε-amino surrogate. See Fontana et al. 2008.

In a typical transglutaminase-mediated conjugation, the glutamine residue is located on the antibody, while the amino group is located on the linker-partner molecule moiety, as shown below:

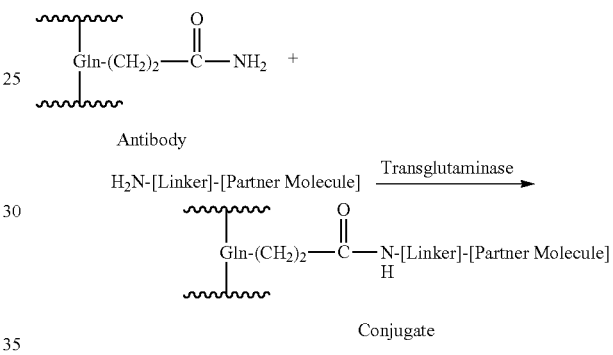

The location of a glutamine residue on a polypeptide chain has a large effect on its availability as an amine acceptor. Normally, none of the glutamine residues on an antibody are available and some modification of the antibody is necessary to make them available. Typically, an antibody is glycosylated at asparagine 297 (N297) of the heavy chain (N-linked glycosylation). Jeger et al. 2010 discovered that deglycosylation of the antibody, either by eliminating the glycosylation site through an N297A substitution or post-translation enzymatic deglycosylation, renders nearby glutamine 295 (Q295) available for transamidation by *S. mobaraensis* transglutaminase. They further showed that an N297Q substitution not only eliminates glycosylation, but also introduces a second glutamine residue (at position 297) that too is an amine acceptor. Thus, simple deglycosylation generates two transglutaminase reactive glutamine residues per antibody (one per heavy chain, at Q295), while an antibody with an N297Q substitution generates four such glutamine residues (two per heavy chain, at positions Q295 and Q297).

In addition to the N297A and N297Q substitutions disclosed by Jeger et al. 2010, there have been other disclosures on modifying an antibody or another protein to make it a substrate for transglutaminase.

(a) Strop et al. 2017 and Farias et al. 2016 disclose antibody Fc regions engineered with glutamine-containing tags such as LLQGG, LSLSQG, GGGLLQGG, GLLQG, etc., where the glutamine in the tag can act as an amine acceptor and be positioned at various places of an antibody heavy or light chain, including the carboxy termini thereof (b) Chen et al. 2005 discloses the modification of a protein with the tag QSKVX, where X is L or I, which protein can then be conjugated with transglutaminase.
(c) Fischer et al. 2015 discloses the incorporation into an antibody fragment lacking an Fc domain a glutamine (Q) containing tag of the formula (Q)-NH—(C)—X-L-(V—(Y-(M or Z)$_z$)$_q$)$_r$ (d) Rao-Naik et al. 2018 discloses appending glutamine-containing heavy chain C-terminal extensions to an antibody to render it transglutaminase-reactive.

In an approach complementary to modifying an antibody to make it transglutaminase-reactive, Rao-Naik et al. 2017 discloses modifying transglutaminase to make it capable of conjugating to a wild-type antibody.

There also have been studies on the substrate specificity of transglutaminase using small peptide-containing molecules: Ando et al. 1989, Kamiya et al. 2011, Ohtsuka et al. 2000.

Other disclosures relating to conjugation of antibodies or other proteins using transglutaminase are: Bregeon 2016, Bregeon et al. 2016, Bregeon et al. 2017, Dennler et al. 2014, Innate Pharma 2013, Lin et al. 2006, Mero et al. 2009, Mindt et al. 2008, Sato 2002, Sato et al. 2001, Schibli et al. 2007, and Sugimura et al. 2007.

It is also known to attach cysteine-containing terminal extensions to an antibody for the purpose of effecting conjugation via Michael addition to a maleimide group. Liu et al. 2014 disclose attaching such extensions to the C-terminus of a heavy chain. Babcook et al. 2017 disclose attaching such extensions to the C-terminus of a light chain.

Full citations for the documents cited herein by first author or inventor and year are listed at the end of this specification.

BRIEF SUMMARY OF THE DISCLOSURE

The location of the conjugation site can affect the stability and pharmacokinetics of a conjugate. Strop et al. 2013. Thus, it is desirable to provided alternative conjugation sites and conjugate structures to diversify the options available for the development of biologics.

This specification discloses antibodies having C-terminal glutamine-containing extensions on a light chain for conjugation with transglutaminase. In one embodiment, there is provided a full length antibody having on the C-terminus (carboxy terminus) of a light chain thereof a glutamine-containing extension comprising an amino acid sequence selected from the group consisting of SEQ ID NO:1, NO:2, NO:3, NO:4, NO:5, NO:6, NO:7, NO:8, NO:9, NO:10, NO:11, NO:12, NO:13, NO:14, NO:15, NO:16, NO:17, NO:18, NO:19, NO:20, NO:21, NO:22, NO:23, NO:24, NO:25, NO:26, NO:29, NO:30, NO:31, NO:32, NO:33, NO:34, NO:35, NO:36, NO:37, NO:38, NO:39, and NO:40.

In another aspect, this specification provides a conjugate of the formula (IV)

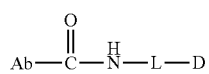
(IV)

wherein
Ab is a full length antibody having on the C-terminus (carboxy terminus) of a light chain thereof a glutamine-containing extension comprising an amino acid sequence selected from the group consisting of SEQ ID NO:1, NO:2, NO:3, NO:4, NO:5, NO:6, NO:7, NO:8, NO:9, NO:10, NO:11, NO:12, NO:13, NO:14, NO:15, NO:16, NO:17, NO:18, NO:19, NO:20, NO:21, NO:22, NO:23, NO:24, NO:25, NO:26, NO:29, NO:30, NO:31, NO:32, NO:33, NO:34, NO:35, NO:36, NO:37, NO:38, NO:39, and NO:40;
L is a linker moiety bonded to Ab via the amide bond

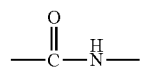

to a glutamine in a glutamine containing extension; and
D is selected from the group consisting of a protein, a radioisotope, an assay agent, and a therapeutic agent.

In another aspect, this specification provides a method of making an antibody conjugate, comprising the steps of
(a) mixing a full length antibody having on the C-terminus (carboxy terminus) of a light chain thereof a glutamine-containing extension comprising an amino acid sequence selected from the group consisting of SEQ ID NO:1, NO:2, NO:3, NO:4, NO:5, NO:6, NO:7, NO:8, NO:9, NO:10, NO:11, NO:12, NO:13, NO:14, NO:15, NO:16, NO:17, NO:18, NO:19, NO:20, NO:21, NO:22, NO:23, NO:24, NO:25, NO:26, NO:29, NO:30, NO:31, NO:32, NO:33, NO:34, NO:35, NO:36, NO:37, NO:38, NO:39, and NO:40 with an amine donor compound comprising a primary amine and a moiety selected from the group consisting of a protein, a radioisotope, an assay agent, and a therapeutic agent, in the presence of a transglutaminase; and
(b) allowing the transglutaminase to catalyze the formation of an amide bond between the side chain carboxamide of a glutamine of the glutamine-containing extension and the primary amine of the amine donor compound, thereby making the antibody conjugate.

In another aspect, this specification provides a method of making an antibody conjugate, comprising the steps of
(a) mixing a full length antibody having on the C-terminus (carboxy terminus) of a light chain thereof a glutamine-containing extension comprising an amino acid sequence selected from the group consisting of SEQ ID NO:1, NO:2, NO:3, NO:4, NO:5, NO:6, NO:7, NO:8, NO:9, NO:10, NO:11, NO:12, NO:13, NO:14, NO:15, NO:16, NO:17, NO:18, NO:19, NO:20, NO:21, NO:22, NO:23, NO:24, NO:25, NO:26, NO:29, NO:30, NO:31, NO:32, NO:33, NO:34, NO:35, NO:36, NO:37, NO:38, NO:39, and NO:40 with a first compound, which first compound is an amine donor compound having a primary amine and a first reactive functional group, in the presence of a transglutaminase;
(b) allowing the transglutaminase to catalyze the formation of an amide bond between the side chain carboxamide of a glutamine of the glutamine-containing extension and the primary amine of the first compound, to make an adduct of the antibody and the first compound;
(c) contacting the adduct with a second compound having a second reactive functional group and a moiety selected from the group consisting of a protein, a radioisotope, an assay agent, and a therapeutic agent; the second reactive functional group being capable of reacting with the first reactive functional group to form a covalent bond therebetween; and (d) allowing the first and second reactive functional groups to react and form a covalent bond therebetween, thereby making the antibody conjugate.

Where moiety (in the first compound or second compound, as the case may be) is a protein, the resultant conjugate is a fusion protein. Where the moiety is a radioisotope, the resultant conjugate can be used for radiation therapy or radioimaging. The moiety can be an assay agent such as a fluorescent label, a deuterated polymer, or a ligand like biotin, in which case the conjugate can be used for diagnosing a medical condition, monitoring of treatment, or analytical applications. Preferably, the moiety is a therapeutic agent (in which case the product is also referred to as an antibody-drug conjugate or ADC), which can be used in medical treatments, especially the treatment of cancer.

BRIEF DESCRIPTION OF THE DRAWING(S)

FIG. 1 shows schematically an antibody light chain having a C-terminus extension (SEQ ID NO:1) as disclosed herein.

Figure 2:
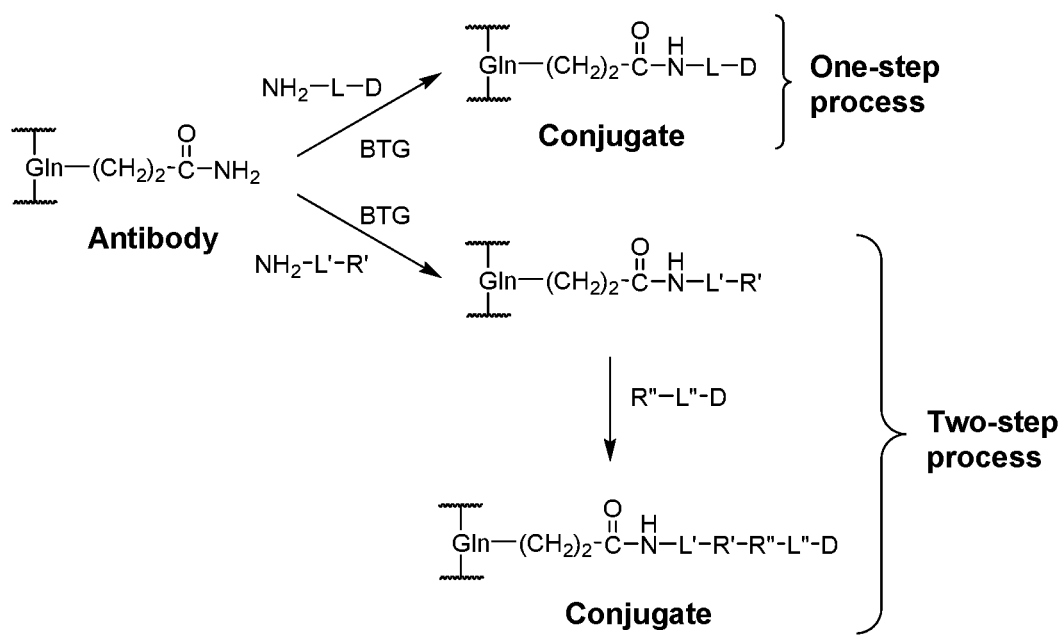

FIG. 2 compares the one- and two-step methods for making conjugates using transglutaminase (BTG).

DETAILED DESCRIPTION OF THE DISCLOSURE

Definitions

"Antibody" means whole antibodies and any antigen binding fragment (i.e., "antigen-binding portion") or single chain variants thereof. A whole antibody is a protein comprising at least two heavy (H) chains and two light (L) chains inter-connected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a $K_D$ of $5 \times 10^{-8}$ M or less, more preferably $1 \times 10^{-8}$ M or less, more preferably $6 \times 10^{-9}$ M or less, more preferably $3 \times 10^{-9}$ M or less, even more preferably $2 \times 10^{-9}$ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology*, 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Preferred antigen binding fragments are Fab, F(ab')$_2$, Fab', Fv, and Fd fragments. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

Unless indicated otherwise—for example by reference to the linear numbering in a SEQ ID NO: listing—references to the numbering of amino acid positions in an antibody heavy or light chain variable region ($V_H$ or $V_L$) are according to the Kabat system (Kabat et al., "Sequences of proteins of immunological interest, 5th ed., Pub. No. 91-3242, U.S. Dept. Health & Human Services, NIH, Bethesda, Md., 1991, hereinafter "Kabat") and references to the numbering of amino acid positions in an antibody heavy or light chain constant region ($C_{H1}$, $C_{H2}$, $C_{H3}$, or $C_L$) are according to the EU index as set forth in Kabat. See Lazar et al., US 2008/0248028 A1, the disclosure of which is incorporated herein by reference, for examples of such usage. Further, the ImMunoGeneTics Information System (IMGT) provides at its website a table entitled "IMGT Scientific Chart: Correspondence between C Numberings" showing the correspondence between its numbering system, EU numbering, and Kabat numbering for the heavy chain constant region.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germ-line immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human anti-body" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

Embodiments

Generally, transglutaminase-mediated preparation of an antibody conjugate can be by a one-step process or a two-step process, as illustrated schematically in FIG. 2. In the one-step process, transglutaminase couples a glutamine carboxamide on the extension, acting as the amine acceptor, and an amine donor compound H$_2$N-L-D, where L is a linker moiety and partner molecule D is a protein, a radioisotope, an assay agent, or a therapeutic agent, to form the conjugate directly. In the two-step process, transglutaminase catalyzes the formation of an initial transamidation adduct between a glutamine carboxamide on the extension, acting as the amine receptor, and first compound (H$_2$N-L'-R'), which is an amine donor compound, where L' is a first linker moiety and R' is a first reactive functional group. Subsequently, the adduct is reacted with a second compound (R"-L"-D), where R" is a second reactive functional group capable of reacting with R', L" is a second linker moiety, and D is as defined above. Sometimes, the one-step process is referred to as the enzymatic process, and the two-step process as the chemoenzymatic process because it entails both a chemical and an enzymatic step. Each of L, L', and L" can be an alkyl chain —(CH$_2$)$_m$— where m is an integer from 2 to 10, inclusive, or can be, especially in the case of L and L", a more complex structure, as discussed below.

The amine donor, whether H$_2$N-L-D or H$_2$N-L'-R', is often used in large excess to suppress undesired transamidation between the glutamine carboxamide and an ε-amino group of an antibody lysine. If the moiety D is expensive or difficult to obtain, the use of a large excess may be impractical. In such instances, the two-step process may be preferable, even though it requires an additional step.

As a demonstration, we conjugated an anti-mesothelin antibody having the same heavy and light chain CDRs as antibody 6A4 of Terrett et al., U.S. Pat. No. 8,268,970 B2 (2012). Its heavy and light chain sequences are provided as SEQ ID NO:27 and SEQ ID NO:28, respectively. Light chain C-terminal extensions having the sequences disclosed below were attached and the antibodies so modified were then conjugated to either compound (A) or compound (B) as the amine donor, using the one-step process.

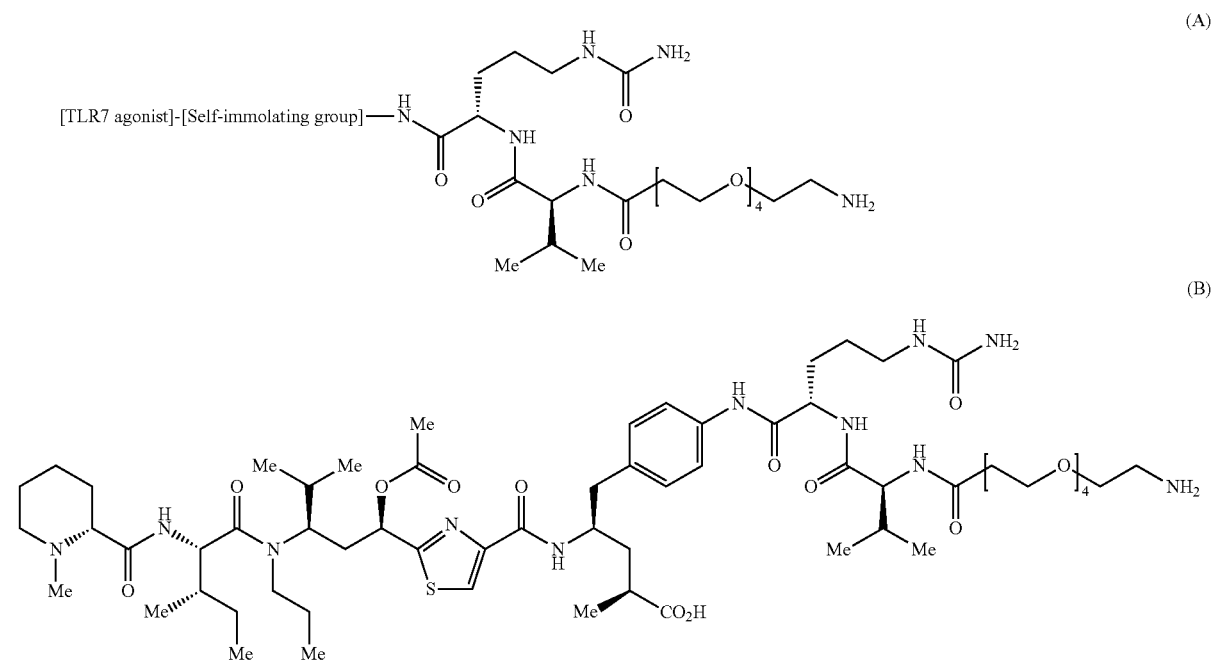

In Compound (A) the therapeutic agent is a Toll-like Receptor 7 (TLR7) agonist, which can be used as an adjuvant for vaccines and immunotherapy agents in treating a variety of conditions. Examples of TLR7 agonists are disclosed in U.S. application Ser. Nos. 16/103,210, 16/103,511, 16/103,581, 16/013,601, and 16/103,619; each filed Aug. 14, 2018; the disclosures of which are incorporated herein by reference. In Compound (B) the therapeutic agent is a tubulysin analog, a cytotoxin that can be used in anti-cancer treatment. The preparation of Compound (B) is disclosed in U.S. Provisional Application Ser. No. 62/688,737, filed Jun. 22, 2018; the disclosure of which is incorporated herein by reference.

In one embodiment, light chain C-terminal extensions disclosed herein have one glutamine. Examples are listed in Table A below, along with the drug-antibody ratio (DAR) of conjugates prepared therefrom. As there are two light chains per antibody, each bearing an extension, the theoretical maximum DAR is 2.0. FIG. 1 shows schematically an antibody light chain having the C-terminal extension of SEQ ID NO:1.

TABLE A

Extensions with One Glutamine

| SEQ ID NO: | Extension Sequence | DAR (Cpd. A) | DAR (Cpd. B) |
|---|---|---|---|
| 1 | GGVLQRAS | 1.99 | 2.0 |
| 2 | GGVLQGAS | 1.84 | 1.6 |
| 3 | GGVLQRPS | 1.96 | 2.0 |
| 4 | GGVLQGPS | 1.97 | 2.0 |
| 5 | GGVLQSPS | 1.94 | 1.77 |
| 6 | GGVLQYAS | 1.87 | 1.7 |
| 7 | GGGGVLQRAS | 1.99 | 2.0 |
| 8 | GGGGVLQGAS | 1.95 | 2.0 |
| 9 | GGGGVLQRPS | 1.99 | 2.0 |
| 10 | GGGGVLQGPS | 1.94 | 2.0 |
| 11 | GGGGVLQSPS | 1.99 | 2.0 |
| 12 | GGGGVLQYAS | 2 | 2.0 |
| 13 | VLQYAS | 0.95 | 0.97 |

In another embodiment, the light chain C-terminal extension have two glutamines. Examples are listed in Table B below, along with the drug-antibody ratio (DAR) of conjugates prepared therefrom. As there are two light chains per antibody, each bearing an extension with two glutamines, the theoretical maximum DAR is 4.0.

TABLE B

Extensions with Two Glutamines

| SEQ ID NO: | Extension Sequence | DAR (Cpd. A) | DAR (Cpd. B) |
|---|---|---|---|
| 14 | GGVLQRQS | 2.37 | 2.05 |
| 15 | GGVLQGQS | 2.04 | 2.04 |
| 16 | GGVLQRQRPS | 2.23 | 2.01 |
| 17 | GGVLQGQGPS | 3.27 | 3.19 |
| 18 | GGVLQSQSPS | 1.86 | 2.01 |
| 19 | GGVLQYQS | 2.90 | 2.60 |
| 20 | GGGGVLQRQS | 2.95 | 2.88 |
| 21 | GGGGVLQGQS | 2.60 | 2.89 |
| 22 | GGGGVLQRQRPS | 2.96 | 2.88 |
| 23 | GGGGVLQGQGPS | 3.72 | 3.71 |
| 24 | GGGGVLQSQSPS | 2.37 | 2.84 |
| 25 | GGGGVLQYQS | 3.32 | 3.58 |
| 26 | VLQYQS | 1.95 | 2.67 |
| 29 | GGVLQVLQS | | 3.0 |
| 30 | GGVLQGVLQS | | 3.8 |
| 31 | GGVLQGGVLQS | | 3.4 |
| 32 | GGVLQVLQGPS | | 2.5 |
| 33 | GGVLQGGQGPS | | 3.0 |
| 34 | GGVLQGGGQGPS | | 3.1 |
| 35 | GGGGVLQVLQS | | 3.2 |
| 36 | GGGGVLQGVLQS | | 4.0 |
| 37 | GGGGVLQGGVLQS | | 4.0 |
| 38 | GGGGVLQVLQGPS | | 3.2 |
| 39 | GGGGVLQGGQGPS | | 3.5 |
| 40 | GGGGVLQGGGQGPS | | 3.3 |

It may be that, in C-terminal extensions having two glutamines, it is beneficial to separate the glutamines from each other further than they are in Table B, by interposing between two and four amino acids between them.

As the C-terminus of a light chain is somewhat buried, it is desirable to provide spacers to make the glutamine in the extension more protruding and accessible to transglutaminase. Such effect can be achieved by using plural glycines (two to four) at the N-terminus of the extension. Referring to Table A, it can be seen that the extension with no glycines (SEQ ID NO:13) leads to a lower DAR than those having two or four glycines.

In one embodiment, the antibody has a light chain C-terminal extension comprising two spacer glycines and one glutamine. Such extensions are exemplified by SEQ ID NO:1, NO:2, NO:3, NO:4, NO:5, and NO:6.

In another embodiment, the antibody has a light chain C-terminal extension comprising four spacer glycines and one glutamine. Such extensions are exemplified by SEQ ID NO:7, NO:8, NO:9, NO:10, NO:11, and NO:12.

In another embodiment, the antibody has a light chain C-terminal extension comprising two spacer glycines and two glutamines. Such extensions are exemplified by SEQ ID NO:14, NO:15, NO:16, NO:17, NO:18, NO:19, NO:29, NO:30, NO:31, NO:32, NO:33, and NO:34.

In another embodiment, the antibody has a light chain C-terminal extension comprising four spacer glycines and two glutamines. Such extensions are exemplified by SEQ ID NO:20, NO:21, NO:22, NO:23, NO:24, NO:25, NO:35, NO:36, NO:37, NO:38, NO:39 and NO:40.

Advantageously, the C-terminal light chain extensions contain a valine-leucine dipeptide (VL) on the N-terminal side of a glutamine.

Antibodies that can be modified and conjugated by the methods of this disclosure include those recognizing the following antigens: mesothelin, prostate specific membrane antigen (PSMA), CD19, CD22, CD30, CD70, B7H3, B7H4 (also known as O8E), protein tyrosine kinase 7 (PTK7), glypican-3, RG1, fucosyl-GM1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., U.S. Pat. No. 8,609,816 B2 (2013; B7H$_4$, also known as O8E; in particular antibodies 2A7, 1G11, and 2F9); Rao-Naik et al., U.S. Pat. No. 8,097,703 B2 (2012; CD19; in particular antibodies 5G7, 13F1, 46E8, 21D4, 21D4a, 47G4, 27F3, and 3C10); King et al., U.S. Pat. No. 8,481,683 B2 (2013; CD22; in particular antibodies 12C5, 19A3, 16F7, and 23C6); Keler et al., U.S. Pat. No. 7,387,776 B2 (2008; CD30; in particular antibodies 5F11, 2H9, and 17G1); Terrett et al., U.S. Pat. No. 8,124,738 B2 (2012; CD70; in particular antibodies 2H5, 10B4, 8B5, 18E7, and 69A7); Korman et al., U.S. Pat. No. 6,984,720 B1 (2006; CTLA-4; in particular antibodies 10D1, 4B6, and 1E2); Vistica et al., U.S. Pat. No. 8,383,118 B2 (2013, fucosyl-GM1, in particular antibodies 5B1, 5B1a, 7D4, 7E4, 13B8, and 18D5) Korman et al., U.S. Pat. No. 8,008,449 B2 (2011; PD-1; in particular antibodies 17D8, 2D3, 4H1, 5C4, 4A11, 7D3, and 5F4); Huang et al., US 2009/0297438 A1 (2009; PSMA. in particular antibodies 1C3, 2A10, 2F5, 2C6); Cardarelli et al., U.S. Pat. No. 7,875,278 B2 (2011; PSMA; in particular antibodies 4A3, 7F12, 8C12, 8A11, 16F9, 2A10, 2C6, 2F5, and 1C3); Terrett et al., U.S. Pat. No. 8,222,375 B2 (2012; PTK7; in particular antibodies 3G8, 4D5, 12C6, 12C6a, and 7C8); Terrett et al., U.S. Pat. No. 8,680,247 B2 (2014; glypican-3; in particular antibodies 4A6, 11E7, and 16D10); Harkins et al., U.S. Pat. No. 7,335,748 B2(2008; RG1; in particular antibodies A, B, C, and D); Terrett et al., U.S. Pat. No. 8,268,970 B2 (2012; mesothelin; in particular antibodies 3C10, 6A4, and 7B1); Xu et al., US 2010/0092484 A1 (2010; CD44; in particular antibodies 14G9.B8.B4, 2D1.A3.D12, and 1A9.A6.B9); Deshpande et al., U.S. Pat. No. 8,258,266 B2 (2012; IP10; in particular antibodies 1D4, 1E1, 2G1, 3C4, 6A5, 6A8, 7C10, 8F6, 10A12, 10A12S, and 13C4); Kuhne et al., U.S. Pat. No. 8,450,464 B2 (2013; CXCR4; in particular antibodies F7, F9, D1, and E2); and Korman et al., U.S. Pat. No. 7,943,743 B2 (2011; PD-L1; in particular antibodies 3G10, 12A4, 10A5, 5F8, 10H10, 1B12, 7H1, 11E6, 12B7, and 13G4); the disclosures of which are incorporated herein by reference.

In respect of conjugates of formula (IV)

(a) D preferably is, in one embodiment, cytotoxic drug.
(b) In another preferred embodiment, D is a TLR7, STING, NLRP3, or RIG-1 agonist.
(c) In a preferred embodiment, L is -(CH$_2$)$_{2-6}$-.
(d) In another preferred embodiment, L is

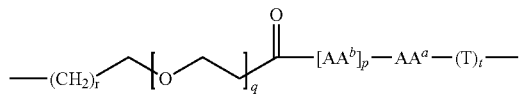

wherein
T is a self-immolating group;
t is 0 or 1;
AA$^a$ and each AA$^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;
p is 1, 2, 3, or 4;
q is 0, 1, 2, 3, 4, 5, 6, 7, 8, 9, or 10; and
r is 1, 2, 3, 4, or 5.

The one-step and two-step processes for conjugation are now discussed in greater detail.

In a preferred embodiment, amine donor compound in a one-step process is represented by formula (I):

$$H_2N—(CH_2)_{2-6}D \quad (I)$$

where D is a protein, a radioisotope, an assay agent, or a therapeutic agent.

In another preferred embodiment, the amine donor compound for the one-step process has a structure represented by formula (Ia):

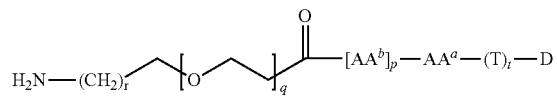

wherein
D is a a protein, a radioisotope, an assay agent, or a therapeutic agent;
T is a self-immolating group;
t is 0 or 1;
AA$^a$ and each AA$^b$ are independently selected from the group consisting of alanine, (3-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;
p is 1, 2, 3, or 4;
q is 0, 1, 2, 3, 4, 5, 6, 7, 8, 9, or 10; and
r is 1, 2, 3, 4, or 5.

In formulae (Ia), (Ia') and (III) (below), -AA$^a$-[AA$^b$]$_p$- represents a polypeptide whose length is determined by the value of p (dipeptide if p is 1, tetrapeptide if p is 3, etc.). AA$^a$ is at the carboxy terminus of the polypeptide and its carboxyl group forms a peptide (amide) bond with an amine nitrogen of D (or T, if present). Conversely, the last AA$^b$ is at the amino terminus of the polypeptide and its α-amino group forms a peptide bond with

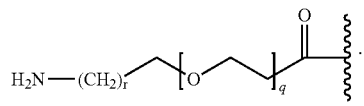

Preferred polypeptides -AA$^a$-[AA$^b$]$_p$- are Val-Cit, Val-Lys, Lys-Val-Ala, Asp-Val-Ala, Val-Ala, Lys-Val-Cit, Ala-Val- Cit, Val-Gly, Val-Gln, and Asp-Val-Cit, written in the conventional N-to-C direction, as in $H_2N$-Val-Cit-$CO_2H$). More preferably, the polypeptide is Val-Cit, Val-Lys, or Val-Ala. Preferably, a polypeptide -$AA^a$-$[AA^b]_p$- is cleavable by an enzyme found inside the target cell, for example a cathepsin and especially cathepsin B, or an enzyme in the environs of the target organ or tissue.

If the subscript q is other than 0, compound (Ia) contains a poly(ethylene glycol) (PEG) group, which can advantageously improve the solubility of compound (Ia), facilitating conjugation to the antibody—a step that is performed in aqueous media. Also, a PEG group can serve as a spacer between the antibody and the peptide -$AA^a$-$[AA^b]_p$—, so that the bulk of the antibody does not sterically interfere with action of a peptide-cleaving enzyme.

As indicated by the subscript t equals 0 or 1, a self-immolating group T is optionally present. A self-immolating group is one such that cleavage from $AA^a$ or $AA^b$, as the case may be, initiates a reaction sequence resulting in the self-immolating group disbonding itself from D and freeing the latter to exert its therapeutic function. When present, the self-immolating group T preferably is a p-aminobenzyl oxycarbonyl (PABC) group, whose structure is shown below, with an asterisk (*) denoting the end of the PABC bonded to an amine nitrogen of drug D and a wavy line ( ~~~~ ) denoting the end bonded to the polypeptide -$AA^a$-$[AA^b]_p$—. The PABC group can be substituted, as disclosed in U.S. Provisional Application Ser. No. 62/677,307, filed May 29, 2018.

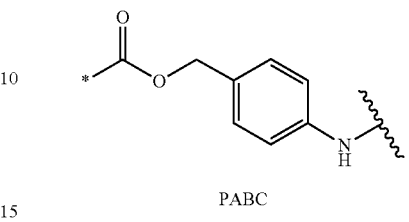

PABC

Another self-immolating group that can be used is a substituted thiazole, as disclosed in Feng, U.S. Pat. No. 7,375,078 B2 (2008).

Compounds (A) and (B) illustrate the design of amine donor compounds according to formula (Ia), with the arrangement of their various elements as shown. Compound (A), but not compound (B), comprises a self-immolating group.

(A)

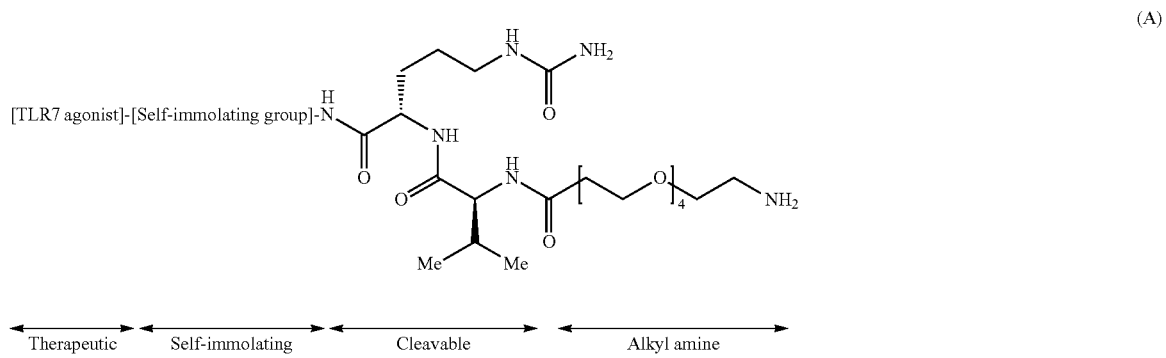

(B)

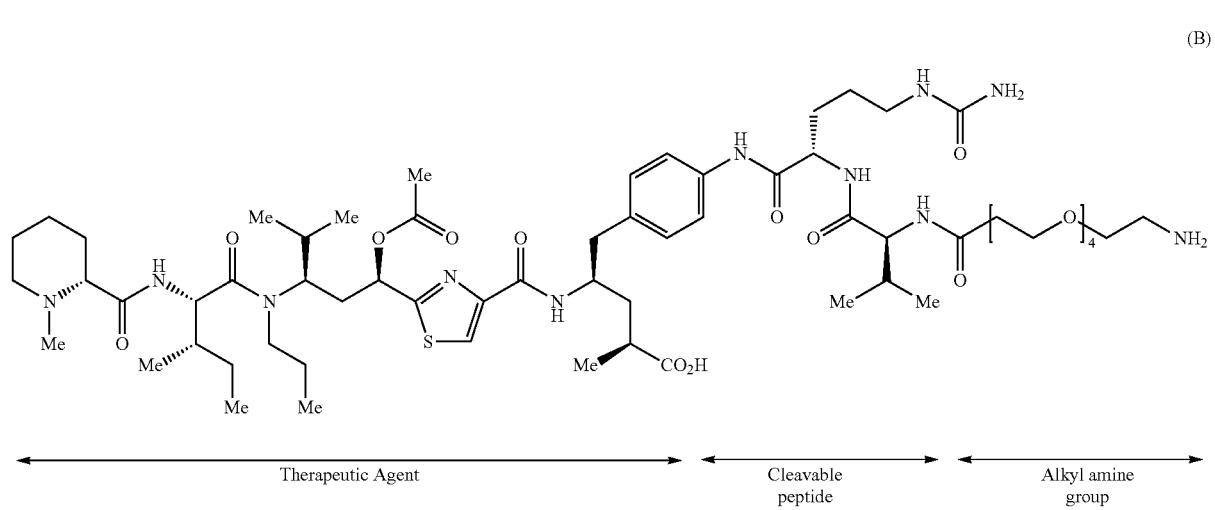

In a two-step conjugation, many combinations of groups R' and R" can be used. Suitable combinations of R' and R" (or, vice-versa, R" and R') include:

(a) a maleimide group and a sulfhydryl group, to form a Michael addition adduct, as in

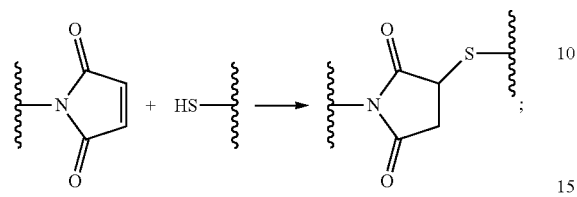

(b) a dibenzocyclooctyne group and an azide group, to form a cycloaddition product via "click" chemistry, as in

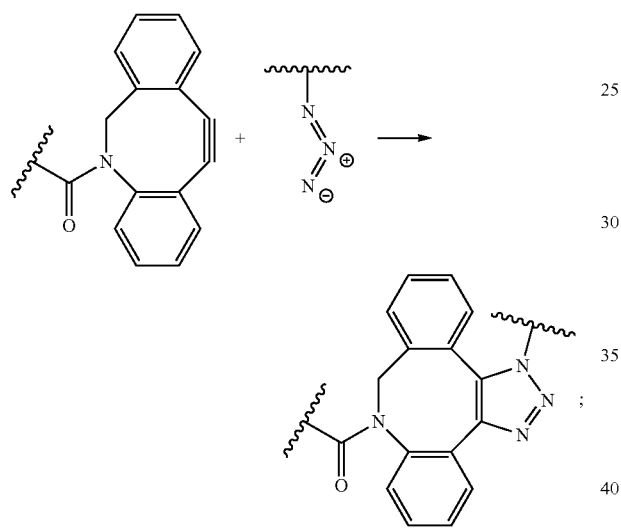

(c) an N-hydroxysuccinimide ester and an amine, to form an amide, as in

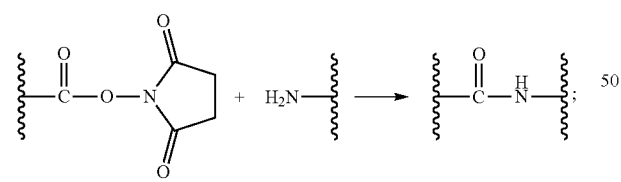

and (d) an aldehyde or ketone (where "alkyl" preferably is C1-3 alkyl) and a hydroxylamine, to form an oxime, as in

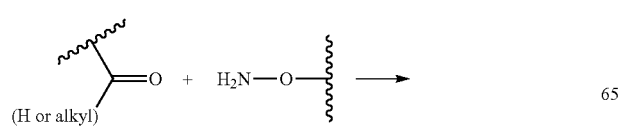

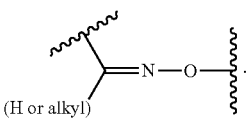
(H or alkyl)

Thus, R' can be selected from

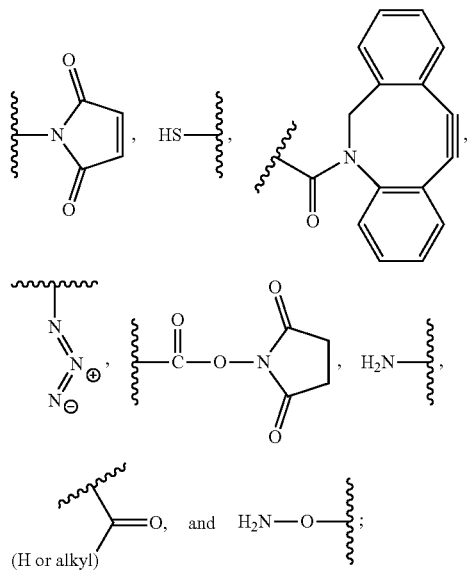

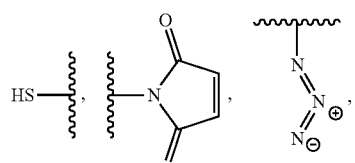
(H or alkyl)

while, reciprocally, R" can be selected from

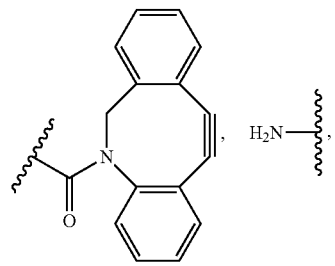

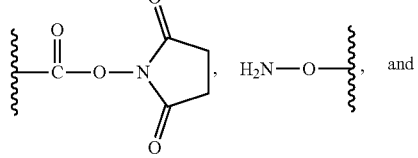

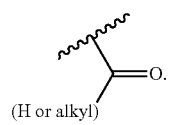
(H or alkyl)

A suitable amine donor first compound for the two-step process is depicted in formula (II)

(II)

where R' is as defined above and preferably is

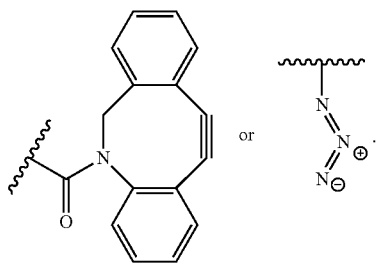

A corresponding suitable compound R"-L"-D is shown in formula (III)

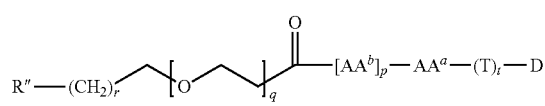

(III)

where R" is as defined above and preferably is

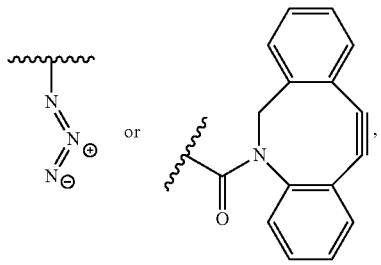

and r, q, $AA^b$, p, $AA^a$, T, t, and D are as defined above in respect of formula (Ia).

In the instance where the conjugate is intended for use in cancer treatment, the therapeutic agent can be a cytotoxic drug that causes death of the targeted cancer cell. Cytotoxic to drugs that can be used in conjugates include the following types of compounds and their analogs and derivatives:

(a) enediynes such as calicheamicin (see, e.g., Lee et al., J. Am. Chem. Soc. 1987, 109, 3464 and 3466) and uncialamycin (see, e.g., Davies et al., WO 2007/038868 A2 (2007); Chowdari et al., U.S. Pat. No. 8,709,431 B2 (2012); and Nicolaou et al., WO 2015/023879 A1 (2015));

(b) tubulysins (see, e.g., Domling et al., U.S. Pat. No. 7,778,814 B2 (2010); Cheng et al., U.S. Pat. No. 8,394,922 B2 (2013); and Cong et al., U.S. Pat. No. 8,980,824 B2 (2015));

(c) DNA alkylators such as analogs of CC-1065 and duocarmycin (see, e.g., Yang et al., US 2018/0051031 A1 (2018); Boger, U.S. Pat. No. 6,545,530 B1 (2003); Sufi et al., U.S. Pat. No. 8,461,117 B2 (2013); and Zhang et al., U.S. Pat. No. 8,852,599 B2 (2014));

(d) epothilones (see, e.g., Vite et al., US 2007/0275904 A1 (2007) and U.S. RE42930 E (2011));

(e) auristatins (see, e.g., Senter et al., U.S. Pat. No. 6,844,869 B2 (2005) and Doronina et al., U.S. Pat. No. 7,498,298 B2 (2009));

(f) benzodiazepine dimers (see, e.g., Zhang et al., U.S. Pat. No. 9,527,871 B2 (2016); Zhang et al., U.S. Pat. No. 9,688,694 B2 (2017); McDonald et al., U.S. Pat. No. 9,526,801 B2 (2016); Howard et al., US 2013/0059800 A1(2013); US 2013/0028919 A1 (2013); and WO 2013/041606 A1 (2013)); and (g) maytansinoids such as DM1 and DM4 (see, e.g., Chari et al., U.S. Pat. No. 5,208,020 (1993) and Amphlett et al., U.S. Pat. No. 7,374,762 B2 (2008)).

In one embodiment, the cytotoxic drug is a DNA alkylator, a tubulysin, an auristatin, a benzodiazepine dimer, an enediyne, or a maytansinoid. Specific examples are, by way of illustration and not of limitation,

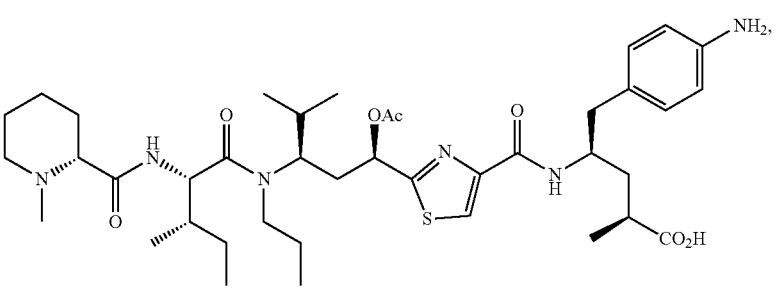

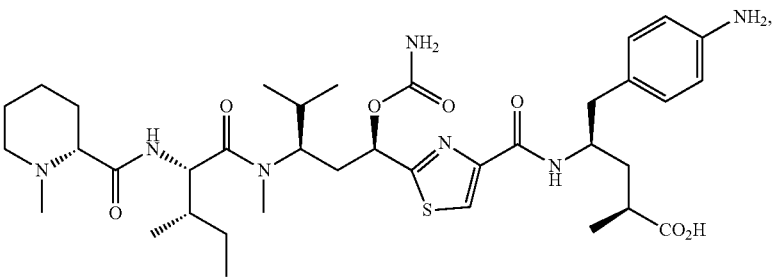

-continued

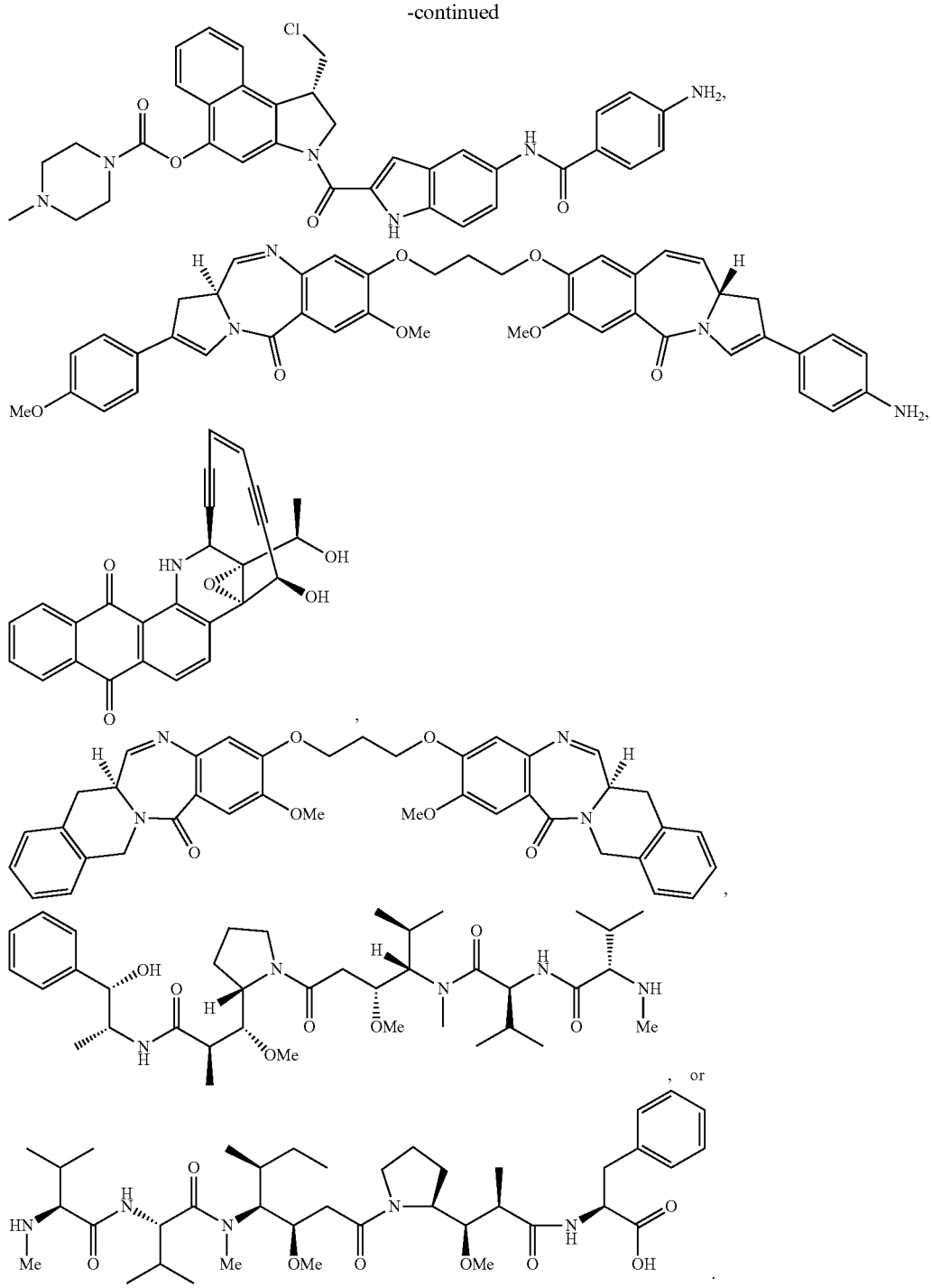

The immune system has receptors whose natural ligands are pathogen-associated molecular patterns (PAMPs). The binding of a PAMP to its cognate receptor activates the immune system to defend against an infection by the associated pathogen. Additionally, these receptors also can be activated by synthetic agonists that have an adjuvant effect on the action of vaccines and immunotherapy agents in treating a variety of conditions other than actual pathogen infection. Immuno-oncology agents such as ipilimumab, nivolumab, and pembrolizumab in particular can benefit from this adjuvant effect. Receptors that can be activated by synthetic agonists include TLR3, TLR7, TLR9 (Toll-like receptor-3, -7, and -9, respectively), STING (STimulator of INterferon Genes; also known as MPYS, TMEM173, MITA or ERIS), NLRP3 (NOD-like receptor protein 3), and RIG-I (retinoic acid inducible gene I). Thus, in an alternative embodiment, the therapeutic agent is a TLR3, TLR7, TLR9, STING, NLRP3, or RIG-I agonist. In particular, the therapeutic agent can be a TLR7 agonist as disclosed in Poudel et al., US 2019/0055243 A1 (2019); Young et al., US 2019/0055244 A1 (2019); Poudel et al., US 2019/0055245 A1 (2019); He et al., US 2019/0055246 A1 (2019); He et al., US 2019/0055247 A1 (2019); and Purandare et al., PCT Application PCT/US2019/028697, filed Apr. 23, 2019.

The aforementioned therapeutic agents can be used in conjugates made by either the one-step or two-step process.

Examples

The practice of this invention can be further understood by reference to the following examples, which are provided by way of illustration and not of limitation.

Example 1—Preparation of Modified Antibodies

ExpiCHO cells were used to express the antibodies. The ExpiCHO cells were grown in ExpiCHO medium at 37° C., 8% $CO_2$ atmosphere in plastic flasks. The expression vector for the heavy chain and light chain were mixed in OptiMEM, added PEI solution in OptiMEM, and resulting PEI/DNA complex was incubated at room temperature for 30 min before adding to the cells. 24 hrs after transfection, Feed B and VPA were added to the cells and the cells were kept at 37° C. with agitation. After 7 days, the culture supernatant was harvested by centrifugation and filtration. The supernatant was purified with MabSelect SuRe LX resin. Briefly, cell supernatant was incubated with resin overnight at 4° C., washed with 10 CV of PBS, followed by elution with 4 CV of 0.1 M citrate pH 3.5, immediately neutralized with 1/10 volume of 1 M tris pH 8.

Example 2—Conjugation of Modified Antibodies

Conjugation of an antibody modified as described herein with an amine donor using transglutaminase was performed by the protocol listed below. We used dispase activate BTGase with V651 and Y75F point mutations. It was dialyzed it into 50 mM sodium acetate pH5.5 from formulation (buffer 20 mM acetate, 10% glycerol pH4) before use.

The antibody, at ~2 mg/mL, in 50 mM Tris-HCl, pH 8.0, or 20 mM Histidine, 50 mM Imidizaole, 10% sucrose, pH ~7.8 was reacted with 10-fold molar per site excess of the amine donor in the presence of 0.2 molar excess of transglutaminase per antibody. The reaction was allowed to proceed overnight at 37° C. with continuous gentle mixing.

The antibody drug conjugate was 0.2 µm filtered and purified using a mAb Select SuRe™ column (GE Healthcare). The conjugate was loaded onto the column pre-equilibrated with 50 mM Tris-HCl, pH 8.0 and washed with 10 CV (column volumes) of equilibrating buffer followed by 10 CV of 50 mM Tris-HCl, 17% acetonitrile, pH 8.0 to remove unreacted amine donor. The column was re-equilibrated with 50 mM Tris-HCl, pH 8.0 before elution with 0.1 M citrate, pH 3.5 in 1 mL fractions and neutralized with 1/10 of elution volume with 1 M Tris, pH 8.0. The desired fractions are dialyzed in formulation buffer 20 mM Histidine, 10% Sucrose, pH 6.0 and analyzed by LC-MS (ESI-QTOF), RP-HPLC and SDS-PAGE for purity and Drug to Antibody Ratio (DAR).

Example 3—Analysis of Conjugated Modified Antibodies

The antibody at 5 mg/mL in 50 mM imidazole, 10% sucrose, pH 8 was reacted with 10-fold molar per site of the amine donor in the presence of 0.2 molar excess of recombinant bacterial transglutaminase per antibody. After overnight incubation at 37° C. with continuous gentle mixing, the reaction mixture was analyzed by LC-MS (ESI-QTOF) for DAR evaluation.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the following references cited in abbreviated fashion by first author (or inventor) and date earlier in this specification are provided below. Each of these references is incorporated herein by reference for all purposes.

Ando et al., *Agri. Biol. Chem.* 1989, 53, 2613, "Purification and Characteristics of a Novel Transglutaminase Derived from Microorganisms."
Babcook et al., US 2017/0008970 (2017).
Bregeon, US 2016/0114056 A1 (2016).
Bregeon et al., U.S. Pat. No. 9,427,478 B2 (2016).
Bregeon et al., U.S. Pat. No. 9,717,803 B2 (2017).
Chen et al., US 2005/0136491 A1 (2005).
Dennler et al., *Bioconjug. Chem.* 2014, 25, 569, "Transglutaminase-Based Chemo-Enzymatic Conjugation Approach Yields Homogeneous Antibody-Drug Conjugates."
Farias et al., US 2016/0193356 A1 (2016).
Fischer et al., US 2015/0284713 A1 (2015).
Fontana et al., *Adv. Drug Deliv. Rev.* 2008, 60, 13, "Site-Specific modification and PEGylation of pharmaceutical proteins mediated by transglutaminase."
Gerber et al., *Nat. Prod. Rep.* 2013, 30, 625, "The antibody-drug conjugate: an enabling modality for natural product-based cancer therapies."
Innate Pharma, "A New Site Specific Antibody Conjugation Using Bacterial Transglutaminase," presentation at ADC Summit, San Francisco, Calif., Oct. 15, 2013.
Jeger et al., *Angew. Chem. Int. Ed.* 2010, 49, 9995, "Site-Specific and Stoichiometric Modification of Antibodies by Bacterial Transglutaminase."
Kamiya et al., US 2011/0184147 A1 (2011).
Lin et al., *J. Am. Chem. Soc.* 2006, 128, 4542, "Transglutaminase-Catalyzed Site-Specific Conjugation of Small-Molecule Probes to Proteins in Vitro and on the Surface of Living Cells."
Liu et al., U.S. Pat. No. 8,865,875 B2 (2014).
Mero et al., *Bioconjug. Chem.* 2009, 20, 384, "Transglutaminase-Mediated PEGylation of Proteins: Direct Identification of the Sites of Protein Modification by Mass Spectrometry Using a Novel Monodisperse PEG."

Mindt et al., *Bioconjug. Chem.* 2008, 19, 271, "Modification of Different IgG1 Antibodies via Glutamine and Lysine using Bacterial and Human Tissue Transglutaminase."
Ohtsuka et al., *Biosci. Biotechnol. Biochem.* 2000, 64, 2608, "Comparison of Substrate Specificities of Transglutaminases Using Synthetic Peptides as Acyl Donors."
Rao-Naik et al., WO 2017/059158 A1 (2017).
Rao-Naik et al., US 2018/0037921 A1 (2018).
Sato, *Adv. Drug Deliv. Rev.* 2002, 54, 487, "Enzymatic procedure for site-specific pegylation of proteins."
Sato et al., U.S. Pat. No. 6,322,996 B1 (2001).
Schibli et al., US 2007/0184537 A1 (2007).
Smith et al., US 2019/0099505 A1 (2019).
Strop et al., *Chemistry & Biology* 2013, 20, 161, "Location Matters: Site of Conjugation Modulates Stability and Pharmacokinetics of Antibody Drug Conjugates."
Strop et al., U.S. Pat. No. 9,676,871 B2 (2017).
Sugimura et al., *J. Biotechnol.* 2007, 131, 121, "Novel site-specific immobilization of a functional protein using a preferred substrate sequence for transglutaminase 2."

What is claimed is:

1. A full length antibody having on the C-terminus of a light chain thereof a glutamine-containing extension comprising an amino acid sequence selected from the group consisting of SEQ ID NO: 1, NO: 2, NO: 3, NO: 4, NO: 5, NO: 6, NO: 7, NO: 8, NO: 9, NO: 10, NO: 11, NO: 12, NO: 13, NO: 14, NO: 15, NO: 16, NO: 17, NO: 18, NO: 19, NO: 20, NO: 21, NO: 22, NO: 23, NO: 24, NO: 25, NO: 26, NO: 29, NO: 30, NO: 31, NO: 32, NO: 33, NO: 34, NO: 35, NO: 36, NO: 37, NO: 38, NO: 39, and NO: 40.

2. A full length antibody according to claim 1, wherein the extension has an amino acid sequence selected from the group consisting of SEQ ID NO: 1, NO: 2, NO: 3, NO: 4, NO: 5, and NO: 6.

3. A full length antibody according to claim 1, wherein the extension has an amino acid sequence selected from the group consisting of SEQ ID NO: 7, NO: 8, NO: 9, NO: 10, NO: 11, and NO: 12.

4. A full length antibody according to claim 1, wherein the extension has an amino acid sequence selected from the group consisting of SEQ ID NO: 14, NO: 15, NO: 16, NO: 17, NO: 18 and NO: 19.

5. A full length antibody according to claim 1, wherein the extension has an amino acid sequence selected from the group consisting of SEQ ID NO: 20, NO: 21, NO: 22, NO: 23, NO: 24, and NO: 25.

6. A full-length antibody according to claim 1, wherein the glutamine-containing extension has a valine-leucine (VL) on the N-terminal side of a glutamine.

7. A conjugate of the formula (IV)

$$\text{Ab} - \overset{\overset{\displaystyle O}{\|}}{C} - \overset{H}{N} - L - D \quad \text{(IV)}$$

wherein

Ab is a full length antibody having on the C-terminus (carboxy terminus) of a light chain thereof a glutamine-containing extension comprising an amino acid sequence selected from the group consisting of SEQ ID NO: 1, NO: 2, NO: 3, NO: 4, NO: 5, NO: 6, NO: 7, NO: 8, NO: 9, NO: 10, NO: 11, NO: 12, NO: 13, NO: 14, NO: 15, NO: 16, NO: 17, NO: 18, NO: 19, NO: 20, NO: 21, NO: 22, NO: 23, NO: 24, NO: 25, NO: 26, NO: 29, NO: 30, NO: 31, NO: 32, NO: 33, NO: 34, NO: 35, NO: 36, NO: 37, NO: 38, NO: 39, and NO: 40;

L is a linker moiety bonded to Ab via the amide bond $$-\overset{\overset{\displaystyle O}{\|}}{C} - \overset{H}{N} -$$

to a glutamine in a glutamine containing extension; and

D is selected from the group consisting of a protein, a radioisotope, an assay agent, and a therapeutic agent.

8. A conjugate according to claim 7, wherein D is a therapeutic agent, and the therapeutic agent is a cytotoxic drug.

9. A conjugate according to claim 7, wherein D is a TLR3 agonist, TLR7 agonist, TLR9 agonist, STING agonist, NLRP3 agonist, or RIG-I agonist.

10. A conjugate according to claim 7, wherein L is $-(CH_2)_{2-6}-$.

11. A conjugate according to claim 7, wherein L is $$-(CH_2)_r - \left[ O \right]_q - [AA^b]_p - AA^a - (T)_t - \quad \text{(Ia')}$$

wherein

T is a self-immolating group;

t is 0 or 1;

$AA^a$ and each $AA^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

p is 1, 2, 3, or 4;

q is 0, 1, 2, 3, 4, 5, 6, 7, 8, 9, or 10; and r is 1, 2, 3, 4, or 5.

12. A method of making an antibody conjugate, comprising the steps of
(a) mixing a full length antibody having on the C-terminus (carboxy terminus) of a light chain thereof a glutamine-containing extension comprising an amino acid sequence selected from the group consisting of SEQ ID NO: 1, NO: 2, NO: 3, NO: 4, NO: 5, NO: 6, NO: 7, NO: 8, NO: 9, NO: 10, NO: 11, NO: 12, NO: 13, NO: 14, NO: 15, NO: 16, NO: 17, NO: 18, NO: 19, NO: 20, NO: 21, NO: 22, NO: 23, NO: 24, NO: 25, NO: 26, NO: 29, NO: 30, NO: 31, NO: 32, NO: 33, NO: 34, NO: 35, NO: 36, NO: 37, NO: 38, NO: 39, and NO: 40 with an amine donor compound comprising a primary amine and a moiety selected from the group consisting of a protein, a radioisotope, an assay agent, and a therapeutic agent, in the presence of a transglutaminase; and
(b) allowing the transglutaminase to catalyze the formation of an amide bond between the side chain carboxamide of a glutamine of the glutamine-containing extension and the primary amine of the amine donor compound, thereby making the antibody conjugate.

13. A method according to claim 12, wherein the amine donor compound has the structure

$$H_2N-L-D$$

wherein L is a linker moiety and D is a protein, a radioisotope, an assay agent, or a therapeutic agent.

14. A method according to claim 13, wherein the amine donor compound has the structure $$H_2N-(CH_2)_{2-6}D \quad (I)$$

15. A method according to claim 12, wherein the amine donor compound has a structure represented by formula (Ia)

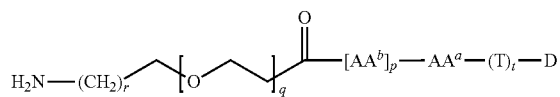

(Ia)

wherein
D is a protein, a radioisotope, an assay agent, or a therapeutic agent;
T is a self-immolating group;
t is 0 or 1;
$AA^a$ and each $AA^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

p is 1, 2, 3, or 4;

q is 0, 1, 2, 3, 4, 5, 6, 7, 8, 9, or 10; and r is 1, 2, 3, 4, or 5.

16. A method according to claim 12, wherein the moiety is a therapeutic agent.

17. A method according to claim 16, wherein the therapeutic agent is a cytotoxic drug.

18. A conjugate according to claim 16, wherein therapeutic agent is a TLR3 agonist, TLR7 agonist, TLR9 agonist, STING agonist, NLRP3 agonist, or RIG-I agonist.

19. A method of making an antibody conjugate, comprising the steps of
(a) mixing a full length antibody having on the C-terminus (carboxy terminus) of a light chain thereof a glutamine-containing extension comprising an amino acid sequence selected from the group consisting of SEQ ID NO: 1, NO: 2, NO: 3, NO: 4, NO: 5, NO: 6, NO: 7, NO: 8, NO: 9, NO: 10, NO: 11, NO: 12, NO: 13, NO: 14, NO: 15, NO: 16, NO: 17, NO: 18, NO: 19, NO: 20, NO: 21, NO: 22, NO: 23, NO: 24, NO: 25, NO: 26, NO: 29, NO: 30, NO: 31, NO: 32, NO: 33, NO: 34, NO: 35, NO: 36, NO: 37, NO: 38, NO: 39, and NO: 40 with a first compound, which first compound is an amine donor compound having a primary amine and a first reactive functional group, in the presence of a transglutaminase;
(b) allowing the transglutaminase to catalyze the formation of an amide bond between the side chain carboxamide of a glutamine of the glutamine-containing extension and the primary amine of the first compound, to make an adduct of the antibody and the first compound;
(c) contacting the adduct with a second compound having a second reactive functional group and a moiety selected from the group consisting of a protein, a radioisotope, an assay agent, and a therapeutic agent; the second reactive functional group being capable of reacting with the first reactive functional group to form a covalent bond therebetween; and
(d) allowing the first and second reactive functional groups to react and form a covalent bond therebetween, thereby making the antibody conjugate.

20. A method according to claim 19, wherein the first compound has the structure $$H_2N-L'-R'$$

wherein L' is a first linker moiety and R' is a first reactive functional group and the second compound has the structure $$R''-L''-D$$

wherein R'' is a second reactive functional group capable of reacting with R', L'' is a second linker moiety, and D is protein, a radioisotope, an assay agent, or a therapeutic agent.

21. A method according to claim 20, wherein R' is selected from

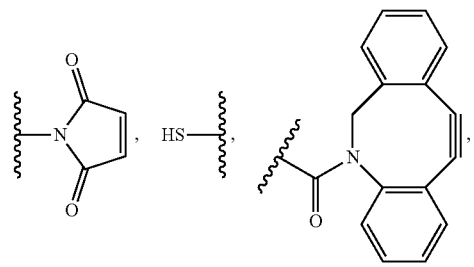

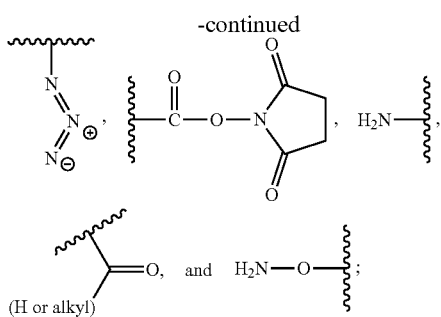

and, reciprocally, R" is selected from

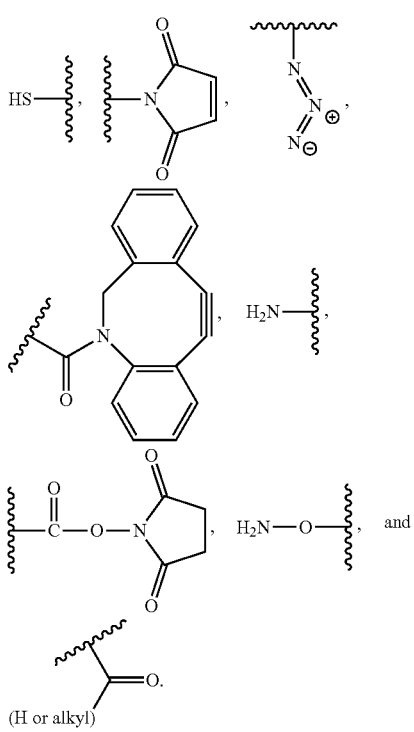

22. A method according to claim 20, wherein the first compound has a structure represented by formula (II)

H$_2$N-(CH$_2$)$_{2-8}$-R'  (II)

and the second compound has a structure represented by formula (III)

wherein
R' is a first reactive functional group;
R" is a second reactive functional group capable of reacting with R';
D is a protein, a radioisotope, an assay agent, or a therapeutic agent;
T is a self-immolating group;
t is 0 or 1;

AA$^a$ and each AA$^b$ are independently selected from the group consisting of alanine, γ-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

p is 1, 2, 3, or 4;

q is 0, 1, 2, 3, 4, 5, 6, 7, 8, 9, or 10; and r is 1, 2, 3, 4, or 5.

23. A method according to claim 22, wherein R' is selected from

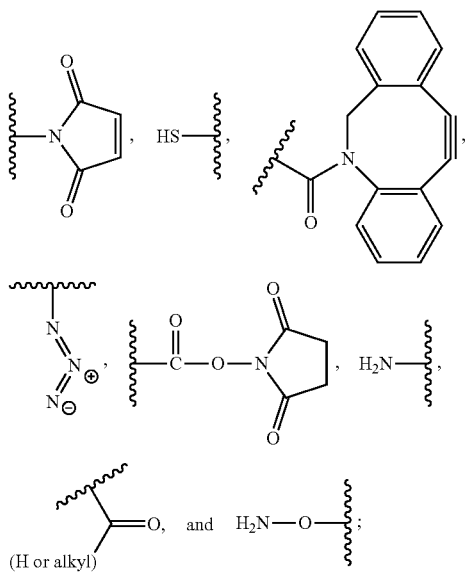

and, reciprocally, R" is selected from

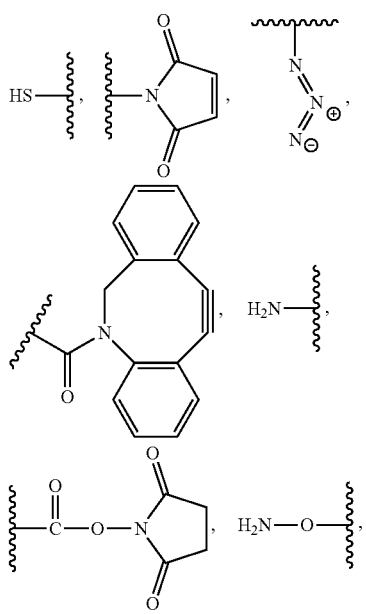

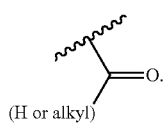
* * * * *

UNITED STATES PATENT AND TRADEMARK OFFICE
CERTIFICATE OF CORRECTION

PATENT NO. : 12,290,570 B2
APPLICATION NO. : 17/297796
DATED : May 6, 2025
INVENTOR(S) : Pavel Strop et al.

It is certified that error appears in the above-identified patent and that said Letters Patent is hereby corrected as shown below:

On the Title Page

Column 2 (item (56) Other Publications):
Line 24 - Delete ""Transflutaminase" and insert -- "Transglutaminase --.
Line 25 - Delete "Indentification" and insert -- Identification --.
Line 31 - Delete ""Comparision" and insert -- "Comparison --.
Line 34 - Delete "Feb. 28, 2020, Feb. 28, 2020," and insert -- Feb. 28, 2020, --.
Line 35 - Delete "Chemisry" and insert -- Chemistry --.
Line 40 - Delete "Mobargensis" and insert -- Mobaraensis --.

In the Claims

Claim 14, Column 41, Line 40:
Delete "$H_2N-(CH_2)_{2-6}D$" and insert -- $H_2N-(CH_2)_{2-6}D$. --.

Claim 18, Column 42, Line 5:
Delete "conjugate" and insert -- method --.

Claim 22, Column 44, Line 2:
Delete "γ-alanine," and insert -- β-alanine, --.

Signed and Sealed this
Fifth Day of August, 2025

Coke Morgan Stewart
*Acting Director of the United States Patent and Trademark Office*